United States Patent [19]

Sowerby

[11] Patent Number: 4,767,552
[45] Date of Patent: Aug. 30, 1988

[54] URAZOLE COMPOSITIONS USEFUL AS ADDITIVES FOR FUNCTIONAL FLUIDS

[75] Inventor: Roger L. Sowerby, Mentor, Ohio

[73] Assignee: The Lubrizol Corporation, Wickliffe, Ohio

[21] Appl. No.: 877,637

[22] Filed: Jun. 23, 1986

[51] Int. Cl.$^4$ ........................................... C10M 133/44
[52] U.S. Cl. .................... 252/46.3; 252/46.4; 252/46.6; 252/47.5; 252/49.6; 252/49.7; 252/49.9; 252/51.5 A; 252/51.5 R; 44/63
[58] Field of Search ................... 548/264; 252/51.5 R, 252/51.5 A, 47.5, 46.4, 46.6, 46.3, 49.9, 49.6, 49.7; 44/63

[56] References Cited

U.S. PATENT DOCUMENTS

| | | | |
|---|---|---|---|
| 3,267,114 | 8/1966 | Wolf | 548/264 |
| 3,621,009 | 11/1971 | Jacobson et al. | 424/269 |
| 4,029,588 | 6/1977 | Koch | 252/48.2 |
| 4,087,534 | 5/1978 | Ovadia et al. | 424/9 |
| 4,088,767 | 5/1978 | Shigematsu et al. | 424/259 |
| 4,249,934 | 2/1981 | Wakabayashi et al. | 71/92 |
| 4,323,687 | 4/1982 | Merten et al. | 548/264 |
| 4,366,320 | 12/1982 | Gilbertson | 548/264 |
| 4,377,694 | 3/1983 | Giesecke et al. | 548/264 |
| 4,386,213 | 5/1983 | Giesecke et al. | 548/264 |
| 4,419,520 | 12/1983 | Rottmaier et al. | 548/264 |
| 4,429,135 | 1/1984 | Giesecke et al. | 548/264 |
| 4,433,085 | 2/1984 | Rottmaier et al. | 524/83 |
| 4,467,099 | 8/1984 | Giesecke et al. | 548/264 |
| 4,481,356 | 11/1984 | Gilbetson | 548/264 |
| 4,551,263 | 11/1985 | Schellhammer et al. | 548/264 |

FOREIGN PATENT DOCUMENTS 0044421 6/1981 European Pat. Off. .
2237687 7/1974 France .

Primary Examiner—Jacqueline V. Howard
Attorney, Agent, or Firm—Robert A. Franks; Denis A. Polyn; Karl Bozicevic

[57] ABSTRACT

Various novel urazole compositions have been discovered that may be generally represented by the formula:

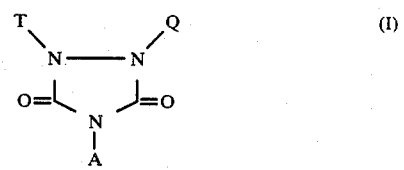

wherein T and Q may be the same or different and represent hydrogen, hydrocarbyl, sulfur, phosphorus, boron, a metal cation, acyloxy hydrocarbyl, imido hydrocarbyl, hydrocarbyl repeating units, hydrocarbyl urazole (I) containing repeating units, an acyl urazole repeating units, an acyl group, or hydrocarbyl acyl containing group, a repeating unit of an acyl group, a repeating unit of a hydrocarbyl acyl containing group, or together form a pi bond between the two nitrogen atoms and A is hydrogen, hydrocarbyl, a hydrocarbyl urazole I group, a repeating unit of a hydrocarbyl containing acyl group or a repeating unit of a hydrocarbyl containing acyl group which is bonded directly to or through a hydrocarbyl group to another urazole (I) group. These compositions may be formulated with functional fluids for use in motorized vehicles.

15 Claims, No Drawings

4,767,552

URAZOLE COMPOSITIONS USEFUL AS ADDITIVES FOR FUNCTIONAL FLUIDS

BACKGROUND OF THE INVENTION

1. Field of the Invention

This invention relates to various heterocyclic nitrogen containing compositions, specifically urazole compositions and derivatives thereof, that are useful as additives for functional fluids, e.g., lubricant compositions and fuels. More specifically, the urazole compositions of the present invention have been found to be highly effective as seal swell agents in automatic transmission fluids (ATF's) and have also been found to be effective as dispersants and friction modifiers in lubricants and fuels.

2. State of the Art

Various urazole compounds and compositions are disclosed in the art for a variety of utilities. For example, in U.S. Pat. No. 4,323,687, a process for preparing 1,2,4-triazolidine-3,5-dione in high yield and with a high degree of purity is disclosed. It is further disclosed in this patent that this urazole specie is a starting material for the preparation of temperature resistant products, e.g., as a cross-linking component in high-temperature-resistant elctrical insulating lacquers and in powder lacquers used for electrostatic powder spray process.

U.S. Pat. Nos. 4,433, 085; 4,429,135; and 4,386,213 disclose various 4-substituted urazole compositions which are substituted at the 4-position with an organic radical which may include a linear or branched aliphatic $C_2$–$C_{30}$ radical. The urazole compositions of these patents are disclosed to be useful as cross-linking agents in temperature-resistant electrical insulating lacquers and in powder lacquers applied by electrostatic powder spraying. They are also disclosed as being useful as flame proofing agents.

U.S. Pat. No. 4,377,694 discloses novel hydroxyalkyl1,2,4-triazolidine-3,5-diones which are useful for the production of rigid or flexible polyurethane foams.

In U.S. Pat No. 4,366,320, 4-substituted phenol-1,2,4-triazoline-3,5-diones and their dihydro analogs are disclosed as analytical reagents useful for preparing adducts of dienes so that the dienes may be assayed by gas liquid chromatography utilizing an electron capture detection system.

Various 1,2-substituted-4-(3',5'-dichlorophenol-)urazole derivatives are disclosed in U.S. Pat. No. 4,088,767 as fungicides for fruit trees, vegetables, rice plants and beans.

U.S. Pat. No. 4,087,534 discloses various halo alkylthio 4-substituted urazoles which are useful as fungicide and bactericidal agents.

Various 1,2-alkylene-4-substituted urazoles and derivatives thereof are disclosed for use as herbicides in U.S. Pat. No. 4,249,934.

U.S. Pat. No. 4,419,520 discloses hydroxyalkyl- and alkoxyalkyl-triazolidine-3,5-dione compounds which are useful flame proofing agents in phenol aldehyde, urea- or melamine formaldehyde resins and may also be used in the production of stoving lacquers.

In U.S. Pat. No. 4,467,099, glycidyl-1,2,4-triazolidine-3,5-diones are disclosed to serve as impregnating agents for textiles, e.g., polyester fibers; as coatings, e.g., painting on glass, metal or wood; as adhesives for various polymer products and the like.

Various diene adducts with triazoline diones are disclosed as novel analytical reagents that may be assayed by gas liquid chromatography utilizing electron capture detection system are disclosed in U.S. Pat. No. 4,481,356.

Various substituted sulfolanes, e.g., where one of the substituents is a 3-alkoxy or 3-alkyl thio group, are disclosed as useful seal swelling agents for machinery, e.g., automatic transmissions, in U.S. Pat. No. 4,029,588.

None of the foregoing disclosures teach the urazole compounds and compositions of the present invention which are useful as seal swell agents for automatic transmission fluids or useful dispersants and friction modifiers in other functional fluids such as lubricants.

SUMMARY OF THE INVENTION

In accordance with the present invention, novel urazole containing compositions have been discovered.

Further, in accordance with the invention, it has been found that the urazole compositions of the invention may be used as additives for functional fluids, e.g., lubricant compositions including automatic transmission fluids and fuel compositions.

Still further in accordance with the invention, functional fluids, including lubricating oils, automatic transmission fluids and fuel compositions, comprising the urazole compositions of the invention are provided.

Still further in accordance with the present invention, urazole compositions useful as seal swell agents for functional fluids, particularly automatic transmission fluids are provided.

Still further in accordance with the present invention, urazole compositions useful as dispersants and friction modifiers for lubricants and fuels are provided.

Still further in accordance with the present invention, concentrates comprising a diluent/solvent and one or more urazole compositions of the present invention are provided for use in functional fluids.

These and other aspects of the invention will become clear to those skilled in the art upon the reading and understanding of the specification.

DETAILED DESCRIPTION OF THE INVENTION

The problem of shrinkage of seals, particularly elastomeric seals, in machinery (e.g., automatic transmissions for motor vehicles) upon contact with functional fluids is of considerable importance since such shrinkage causes leakage of the functional fluid which can lead to defective operation of machinery, or failure to operate at all. (The term "functional fluid" as used herein means a fluid involved in the transmission of energy, such as a lubricant, hydraulic fluid, automatic transmission fluid, heat exchange medium or the like.) To eliminate this problem, it is conventional to include in the functional fluid an additive whose presence therein causes the seal to swell. A number of such additives are known in the art, but their use has several disadvantages. For example, many of them are toxic. Moreover, they most often are used in undesirably large quantities in the functional fluid.

Moreover, the conditions encountered in a large percentage of present-day automobile driving, i.e., the so-called stop-and-go "driving," automobile engines do not attain their most desirable and efficient operating temperatures. As a result, large quantities of oil-insoluble products are formed which eventually find their way into the crankcase by flowing past the piston rings. Since most of these products are oil insoluble, they tend to deposit on the internal parts of the engine, resulting in further inefficient engine operation. In present-day practice, deposition of the oxidation products is minimized by incorporating into lubricating oils detergents/dispersants which keep the oxidation products dispersed.

Unlike a dispersant discussed above, a friction modifier is an additive or combination of additives that has the ability to change the frictional profile of a lubricant/machine system. Usually, the frictional forces between moving lubricant parts are controlled by the viscosity and chemistry of the existing oil film between them. With a straight mineral oil, the static coefficient of friction is higher than the dynamic coefficient of friction. If polar additives are added to the oil, they will coat the metal surfaces and establish an equilibrium between the amounts dissolved in the oil and the ones absorbed or chemisorbed on the metal. The new (coated) metal surfaces will now rub against each other, not only through a thin oil film, but also through their coatings. Therefore, the frictional forces will be different under both breakaway and dynamic conditions. How much they differ will depend, among other factors, on the additives, especially on their molecular configuration and type, as well as on the overall geometry of the rubbing surfaces.

Thus, in transmission clutches with frictional facing material, especially the one of resin-treated paper, friction modification shows frequently as a lower static than dynamic coefficient of friction. In plain metal surfaces, friction modification will show as a sharp drop in the static coefficient of friction and a moderate drop in the dynamic. The curtailing of the usually high static coefficient of friction is referred to in the transmission manufacturers' trade as cutting off the "rooster tail."

In accordance with the present invention various novel urazole compositions have been discovered to be effective seal swell agents, dispersants, dispersant Viscosity Index (V.I., hereinafter) improvers and friction modifiers. In other words, formulating the urazole compositions of the present invention with functional fluids to be used in a motorized vehicle, e.g., an automobile, act to overcome or at least ameliorate the problems discussed above. These urazole compositions may be represented generally by the following formula:

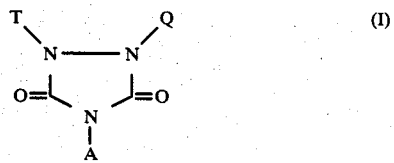

wherein T and Q may be the same or different and represent hydrogen, hydrocarbyl, sulfur, phosphorus, boron, a metal cation, acyloxy hydrocarbyl, imido hydrocarbyl, hydrocarbyl repeating units, hydrocarbyl urazole (I) containing repeating units, an acyl urazole repeating units, an acyl group, or hydrocarbyl acyl containing group, a repeating unit of an acyl group, a repeating unit of a hydrocarbyl acyl containing group, or together form a pi bond between the two nitrogen atoms and A is hydrogen, hydrocarbyl, a hydrocarbyl urazole I group, a repeating unit of a hydrocarbyl containing acyl group or a repeating unit of a hydrocarbyl containing acyl group which is bonded directly to or through a hydrocarbyl group to another urazole (I) group.

It is understood that as represented in the specification and claims when Q and/or T represent sulfur, phosphorus, boron or a metal cation, all the oxidation states of these atoms and radicals or groups bonded thereto are intended to be included in the definition of formula (I) above. For example, when Q and/or T are sulfur, this representation inclues sulfide, sulfate, sulfonate, sulfite as well as other hydrocarbyl or hydrocarbyl repeating units bonded to the sulfur atom(s). This representation also includes one or more urazole (I) groups bonded to the sulfur atom(s). Similarly, if Q and/or T is phosphorus, the radicals phosphate, phosphite, phosphonate and the like are intended to be within the scope of urazole composition represented by formula (I) and other formula set forth in the specification and claims.

As used herein, the terms "hydrocarbyl" or "hydrocarbon-based" denote a radical having a carbon atom directly attached to the remainder of the molecule and having predominantly hydrocarbon character within the context of this invention. Such radicals include the following:

(1) Hydrocarbon radicals; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like, as well as cyclic radicals wherein the ring is completed through another portion of the molecule (that is, any two indicated substituents may together form and alicyclic radical). Such radicals are known to those skilled in the art; examples include methyl, ethyl, butyl, hexyl, octyl, decyl, dodecyl, tetradecyl, octadecyl, eicosyl, cyclohexyl, phenyl and naphthyl (all isomers being included).

(2) substituted hydrocarbon radicals; that is, radicals containing non-hydrocarbon substituents which, in the context of this invention, do not alter the predominantly hydrocarbon character of the radical. Those skilled in the art will be aware of suitable substituents (e.g., halo, hydroxy, alkoxy, carbalkoxy, nitro, alkylsulfoxy).

(3) Hetero radicals; that is, radicals which, while predominantly hydrocarbon in character within the context of this invention, contain atoms other than carbon atoms. Suitable hetero atoms will be apparent to those skilled in the art and include, for example, nitrogen, oxygen, phosphorus and sulfur.

Terms such as "alkyl-based radical", "aryl-based radical" and the like have meaning analogous to the above with respect to alkyl and aryl radicals and the like.

The radicals are usually hydrocarbon and especially lower hydrocarbon, the word "lower" denoting radicals containing up to seven carbon atoms. They are preferably lower alkyl or aryl radicals, most often alkyl.

The term "acyl" as used herein denotes the radical

for all purposes.

The urazole compositions (also named as 1,2,4-triazolidine-3,5-diones) may be prepared by several different methods or by modifications of the same method. Various methods for the preparation of different species of 1,2,4-triazolidine-3,5-diones are described in the previously discussed U.S. Pat. Nos. 4,429,135; 4,386,213; and 4,323,687.

For the purposes of the present invention, the urazole composition may be prepared as represented in the following general reaction scheme I.

Reaction Scheme I

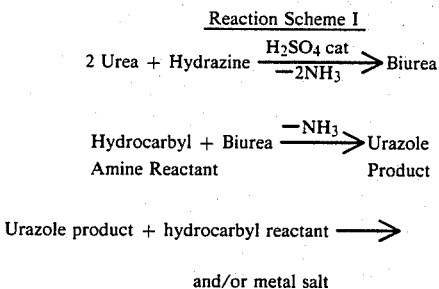

It should be recognized that the above reaction scheme is generalized to encompass all the different urazole species of the present invention. A more specific reaction scheme for the preparation of specific urazole species of the present invention is set out below in reaction scheme II. It is not intended for this reaction scheme II to be limiting upon the scope of the invention where such scope is defined only in the claims.

Reaction Scheme II

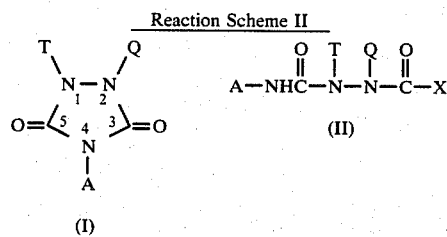

The preparation of (I) above involves first, the formation of a bis acylated hydrazine (II) followed by cyclization (X can be any suitable leaving group (e.g., —OR, —NH$_2$, —NHR)).

Two alternative routes to the 4-substitued urazoles are as follows:

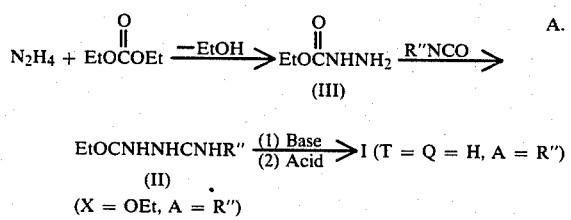

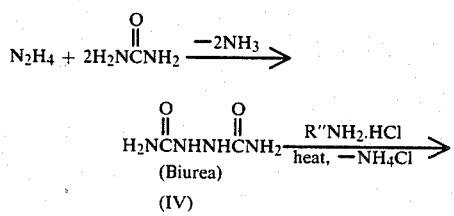

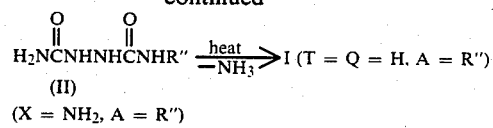

The various substituents and polymer products within the scope of the present invention may be obtained by either modifying the biurea product of step 1 of reaction scheme I or by further reaction of the urazole product of step 2 of the reaction, scheme I, as illustrated in step 3 of the same reaction scheme.

For example, the following urazole derivative

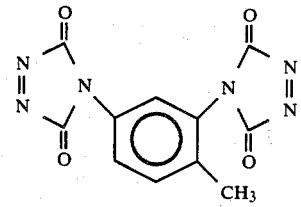

may be obtained the by oxidation of the product from the following reactant (VII).

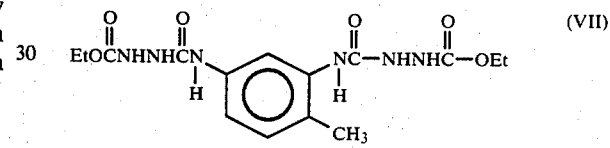

which is obtained from 2,4-toluene diisocyanate and ethyl hydrazine carboxylate.

The above product (VI) may then be reacted with an olefinic material followed by reaction with succinyl chloride to form a polymer which is useful as a dispersant and may be represented by the formula:

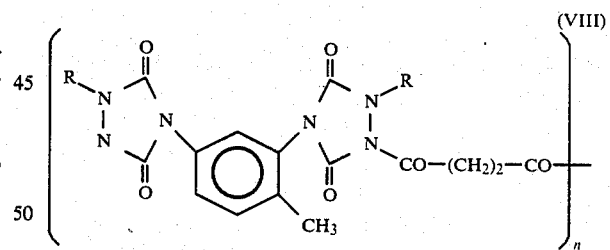

The urazole products or derivatives according to the present invention, in general, fall into the following two categories of products represented by formulas (IX) and (X).

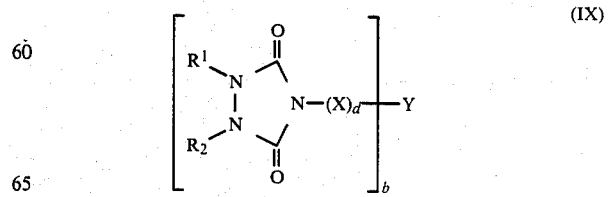

wherein $R^1$ and $R^2$ are the same or different and are hydrogen, hydrocarbyl or together form a pi bond between the two nitrogen atoms, X is hydrocarbyl, hydrocarbylurazole or acylhydrocarbyl, Y is hydrocarbyl or a urazole group or a linking bond to a repeating unit, d is O or at least 1 and b is at least 1.

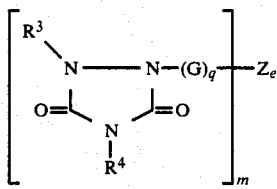
(X)

wherein $R^3$ is independently hydrogen, hydrocarbyl or a linking bond to the group G or Z, $R^4$ is hydrogen, hydrocarbyl acyl, or hydrocarbyl, G is hydrocarbyl, acyl, acyloxy, imido, acyl hydrocarbyl, acyloxy hydrocarbyl, or imido hydrocarbyl, Z is sulfur, phosphorus, boron, a metal cation, or hydrocarbyl, q is 0 or 1, e is 0, 1 or 2 and m is at least 1.

Preferred urazole species represented by formula IX above include urazole compositions wherein $R^1$ and $R^2$ are the same or different and are hydrogen, alkyl or alkenyl of about 8 carbon atoms to about 200 carbon atoms, with the proviso that $R_1$ and $R_2$ is not hot hydrogen, Y is phenyl, oleyl, octyl or isodecyloxypropyl, and d is 0; or wherein $R^1$ is hydrogen, $R^2$ is alkylene of 1 to about 50 carbon atoms, Y is a linking bond with $R^2$, d is 0 and b is at least 1; or wherein $R^1$ and $R^2$ together represent a pi bond between the adjacent nitrogen atoms, Y is alkyl phenylene where said alkyl group is 1 to about 7 carbon atoms, b is 2 and d is 0; or whereinX is arylene, d is 1, Y is alkylene, b is 2 and $R^1$ and $R^2$ are independently hydrogen or hydrocarbyl; or wherein $R^1$ is hydrogen, $R^2$ is hydrogen or hydrocarbyl, Y is arylene or alkylarylene, b is 2 and d is 0; or wherein $R^1$ is hydrogen, $R^2$ is hydrogen or hydrocarbyl, X is arylene, d is 1, Y is alkylene and b is 2; or where $R^1$ is hydrogen or hydrocarbyl, $R^2$ is a linking bond to the repeating unit, Y is a linking bond to the repeating unit, b is at least 2, d is 1 and X is represented by

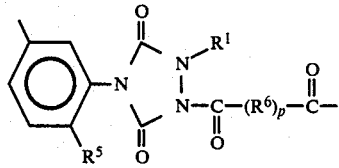

where $R^5$ is hydrocarbyl, $R^6$ is alkylene and p is 0 to about 9.

Preferred urazole species represented by formula (X) above include urazole compositions where $R^3$ is hydrogen or hydrocarbyl, q is 0, Z is Zn, S or boron, e is 1 or 2, and m is 2 and $R^4$ is phenyl, oleyl, octyl, isodecyloxypropyl or ethylhexyl. Other preferred urazole species represented by formula (X) include urazoles where $R_4$ is hydrocarbyl, G is hydrocarbyl acyl or acyl, q is 1, m is at least 2; $R^3$ is a linking bond of the repeating units and e is 0.

The preparation of the compositions of the present invention generally involve the techniques discussed above and techniques similar to those desribed in U.S. Pat. Nos. 4,429,135; 4,386,213; and 4,323,687, previously discussed.

Referring to reaction scheme I above, the biurea product may be purchased from a bulk chemical supplier or prepared from a urea and hydrazine in the presence of an acid catalyst. In the alternative the cyclizable reactant may be prepared from hydrazine reacted with an acyl containing reactant and further reacted with an isocyanate or an equivalent reactant.

The urazole product in step 2 of reaction scheme I may be prepared by heating the reactants, optionally, in the presence of a catalyst.

The particular reactants used to prepare the biurea intermediate product are dependent upon the desired urazole end product. For example, a 4-phenyl urazole may be derived from the reaction of hydrazine with diethyl carbonate which reaction product is further reacted with phenyl isocyanate and cyclized to form the desired 4-phenyl urazole. Alternatively, 4-oleyl urazole may be prepared by the reaction of hydrazine with two (2) moles of urea to from biurea. The biurea intermediate may then be reacted with oleyl amine to produce the desired 4-oleyl urazole.

In accordance with step 3 of reaction Scheme I, the 4-oleyl or 4-phenyl urazole may be further reacted with other reactants to form polymeric products and/or additionally 1- and/or 2-substituted urazoles. For example, the 4-oleyl urazole may be reacted with formaldehyde at about 110° C. to about 50° C. to produce a product represented by the following formula:

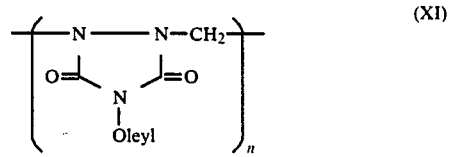
(XI)

wherein n is at least 2.

Likewise, the 4-oleyl urazole may be reacted with itself to form a product represented by the formula:

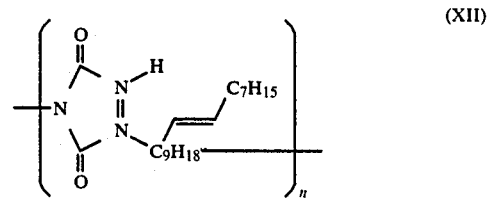
(XII)

wherein n is at least 1. Therefore the potential reactants useful for the preparation of the compositions of the present invention vary widely and include acyl containing reactants, metal salts, phosphorous containing reactants, sulfide reactants, boric acid and its derivatives, isocyanate containing reactants, amine reactants, olefinic containing reactants, acyloxy containing reactants and imido containing reactants. Specific reactants that may be mentioned for illustrative purposes only include tolylene-2,4-disocyanate, ethyl hydrazine carboxylate, methylene di-p-phenyl diisocyanate, methyl amine hydrochloride, octyl amine hydrochloride, adipyl chloride, 2,4-toluene-diisocyanate, boric acid, formaldehyde, paraformaldehyde, dibutylphosphite, sulfur monochloride, diethanolamine, polyisobutylene, zinc oxide, succinyl chloride and the like.

The preparation of various urazole compositions within the scope of the present invention is illustrated in the following examples. While these examples will show one skilled in the art how to operate within the scope of this invention, they are not to serve as a limitation on the scope of the invention where such scope is defined only in the claims. It is pointed out that in the following examples, all percentages and all parts are intended to express percent by weight and parts by weight unless otherwise clearly indicated.

EXAMPLE 1

Preparation of 4-oleyl urazole

Procedure—Step 1—Preparation of biurea $H_2SO_4$ (20 g) was added to a stirred mixture of urea (2640 g) water (500 g) and hydrazine (1000 g). The mixture was heated to reflux with a slow $N_2$ purge. At about 40° C., a clear solution had formed. The material was refluxed at 112°–108° C. for 3 hours. A white precipitate began forming after about 1¼ hr of refluxing.

640 g of water was added to thin the slurry that had formed and reflux at 104°–102° C. was continued for 4 additional hours.

The slurry was cooled to 10° C. The solids were collected by filtration, washed with 1000 g of water, chilled to 10° C. and vacuum dried over night at 50° C.

Yield: 2084 g (88.3%); Analysis: mp=258°–260° C./257°–259° C.

Step 2—Preparation of 4-oleyl urazole from product of 1

HCl (191 g of 37%) was added dropwise to a solution of Armeen® O (472.5 g) in toluene (450 g) at a rate to keep the temperature less than 80° C. The addition took about ½ hour.

The water was then removed by azeotropic distillation. After cooling the solution below reflux, the biurea from above was added. This mixture was then heated to 210° C. The toluene was removed as the temperature increased.

The mixture was heated at 210° C. for 10 hours and then cooled to 150° C. The liquid product was filtered from the $NH_4Cl$ by-product using DD400 filter aid.

The flask and filter pad were then washed with 450 g toluene.

The filtrates were stripped to 150° C. at 4 mm Hg to give desired product.

Yield: 610 g (99.6%); Analysis: %N(Dumas)=11.85/11.97; TAN=155/160; m.p. approx. 120° C.

EXAMPLE 2

Preparation of Ethylhydrazinecarboxylate 100 g of hydrazine and 236 g of diethylcarbonate were were stirred without heat for 20 min (exotherm from 25° C. to 48° C.).

The material was then warmed to 80° C., maintained at this temperature for 3.5 hours and then distilled through a 15 cm vigreaux column at 20 mmHg. The product (173 g) was collected with a bp of 120°–122°.

EXAMPLE 3

Preparation of 4-phenyl urazole 52 g of the product of Example 2 in 550 ml of benzene was cooled in an ice bath and 59.6 g of phenyl isocyanate was added over 45 min with rapid stirring.

After the addition was complete, the ice-bath was removed and the mixture stirred for 2 hrs. at room temperature and then heated at reflux for 2 hrs.

The mixture was cooled to room temperature, filtered and the solids washed with 500 ml benzene.

The solids were vacuum dried overnight to give 108 g of a white powder product. m.p. 152° C.–153° C.

200 ml of 4N KOH and 89.3 g of the above product were warmed to 80° C. for 1.5 hr.

The hot material was then filtered, and the filtrate was acidified to a pH of 4 with 70 ml of conc. HCl. After cooling to room temperature, a white precipitate was collected by filtration.

The precipitate was recrystallized from ethanol giving 53.5 g product after vacuum drying. m.p. 208°–210° C.

EXAMPLE 4

Preparation of 4,4'-tolyene-2,4-di-1-carbethoxysemicarbizide 104 g of the product of Example 2 was added to a solution of 87.1 g of tolyene-2,4-diisocyanate in 1100 ml of benzene over 25 min. in an ice bath.

The mixture was stirred at 38°–40° C. for 1 hr and then at reflux for 2 hr.

The precipitate was collected by filtration after cooling to room temperature and washed with 500 ml of benzene.

The washed precipitate was then vacuum dried to give 190 g of a white powder.

EXAMPLE 5

Preparation of 2,4-Bis-(urazol-4-yl)toluene 95.5 g of the product of Example 4 and 250 ml of 4NKOH were heated to 80° C. for 1.5 hr.

The material was filtered, cooled and 85 ml of concentrated HCl was added.

Water was removed by vacuum rotary evaporation until less than 300 ml of solution remained. After refrigerater cooling for several hours, the resulting precipitate was collected. This material was dissolved in 115 g hot water. The precipitate which formed upon cooling and standing was collected and vacuum dried to give 39.5 g of product.

EXAMPLE 6

Preparation of Methylene di-p-phenyl di-1-carbethoxysemicarbizide 104 g of the product of Example 2 in 1000 ml of toluene was cooled in an ice bath.

A slurry of 125.1 g of methylene di-p-phenyl diisocyanate and 1000 ml of toluene was added over ½ hr. at a rate to keep the temp at 22° C.

The mixture was stirred at room temperature for 2 hr and heated at 80° C. for 2 hr.

After cooling to 40° C., the precipitate was collected, washed with toluene and vacuum dried to produce a dry powder (220 g).

EXAMPLE 7

Preparation of Bis-(p-urazol-4-ylphenyl)methane 114.55 g of the product of Example 6 and 250 ml of 4N KOH was heated to 80° C. for 1.5 hr.

The hot material was filtered, cooled and 85 ml of 12N HCl was added.

The mixture was cooled and a precipitate was collected and vacuum dried to give 87 g of an off white solid.

The solid was slurried in 750 ml of refluxing EtOH for 1 hr, cooled, and the solid was collected and vacuum dried to give the desired product (73.1 g).

EXAMPLE 8

Preparation of 4-Octyl urazol

To 250 ml of toluene and 46 ml of 12M HCl was added 64.6 g of ARMEEN ® 8D over ½ hour with the temperature maintained below 22° C.

The water was then removed by azeotropic distillation along with about 175 ml of toluene.

59 g of the product of Example 1 (Step 1) and 106.5 g of a mineral oil were added and the mixture heated to 220° C. At 185° C. the thick paste became fluid. The material was heated at 220° C. for six hours.

After cooling, the mixture was diluted with toluene and filtered hot.

The filtrate was reduced in volume and cooled. The resulting precipitate was collected by filtration and vacuum dried. 82 g product was obtained which had a m.p. of 137°-139° C.

EXAMPLE 9

Preparation of 1,2 Diacetyl-4-oleyl urazole 100 g of the product of Example 1 was heated to 120° C. under $N_2$. 47.5 g of acetic anhydride was added and the material was heated at 120° C. for 1 hour, 150° C. for 1 hour and 180° C. for 1 hour to form the desired product.

EXAMPLE 10

Preparation of oligomer of 4-oleylurazole with oxalylchloride

To a solution of 35.1 g of the product of Example 1 in 200 ml of toluene at 40° C. was added 12.7 g of the oxalylchloride. The solution was stirred at 40° C. for 3 hours and then at 50° C. for 3 hours.

The material was then heated at reflux for 2 hours. A precipitate began to form after 1½ hours.

The mixture was stripped to 70° C. at 2 mm Hg to give 39.8 of residue.

39 g of the above solid was dissolved in 500 ml dichloromethanol and precipitated by pouring into 100 ml of heptane.

The resulting precipitate was collected and vacuum drived to give 38.5 g of solid product.

GPC molecular weight: Mn=1250; Mw=3450.

EXAMPLE 11

Preparation of oligomer of 4-oleylurazole with adipylchloride

A mixture of 70.2 g of the product of Example 1, 375 ml of toluene and 42.4 g of $Na_2CO_3$ were heated to 80° C.

36.6 g of adipylchloride was then added. After 10 min at 90° C. HCl rapidly evolved. The temperature was raised to 100° C., over 30 min. and maintained at that temperature for 2 hours. The mixture was then refluxed at 110° C. for 4 hours.

The mixture was then filtered and the filtrate was stripped to 150° C. at 3 mmHg to give the desired product (90.5 g). GPC molecular weight: Mn=1400; Mw=3300.

EXAMPLE 12

Preparation of oligomer of 4-Oleylurazoles with 2,4-Toluene-diisocyanate

To a solution of 17.55 g of the product of Example 1 in 200 ml of toluene at 50° C. was added 2,4-toluene diisocyanate and 0.5 g of triethylamine. The material was then heated at 100° C. for 6 hours.

4.5 g of additional triethylamine was added and the material stirred at 40° C. for 3 hours.

A third portion of 5 g of triethylamine was then added and the material stirred at 40° C. for 5 hours and refluxed for 12 hours.

The material was stripped to 150° C. at 1 mmHg to produce desired product (26.8 g).

EXAMPLE 13

Preparation of oligomer from 4-oleylurazole with itself

A solution of 70.2 g of the product of Example 1 in 500 ml of dichloromethane was cooled in an ice bath.

9.2 g of $N_2O_4$ was then added over 40 min at 3°-5° C.

The material was held at 5°-7° C. for 30 min and then warmed to room temperature over 1 hour.

The mixture was stirred at room temperature for 20 hours. The clear red solution became clear and yellow.

The solution was then stripped to 140° C. at 3 mmHg to give final product. GPC molecular weight: Mn=1550; MN=5750.

EXAMPLE 14

Preparation of Borated 4-Oleylurazole 7.75 g of boric acid was added to a solution of the product of Example 1 in 250 ml of toluene and the mixture refluxed with azeotropic removal of water for 2 hours.

After cooling, the material was filtered using diatomaceous earth filter aid.

The filtrate was stripped to 100° C. at 0.5 mmHg to give the desired product.

EXAMPLE 15

Preparation of Bis(4-oleyl urazol-1-yl)disulfide

A solution of 70 g of 4-oleyl urazole (Example 1), 140 ml of toluene and 70 ml of iso-butylalcohol was heated to 40° C.

8 g of NaOH dissolved in 35 ml of water was added and material stirred at 40° C. for ½ hour.

The $H_2O$ was then removed by azeotropic distillation and the solution stripped to 90° C. at 2 mmHg.

A second 140 ml portion of toluene was added to the residue and the material stirred at 40° C. to give a hazy solution. This solution was cooled in an ice bath and 13.5 g of sulfur monochloride was added at 20°-30° C. This material was then slowly heated to 60° C. and held at this temperature for 1 hour.

35 ml of isobutylalcohol and 35 ml of water were added and the material refluxed for 1 hour. The solution was dried by azeotropic distillation, filtered, and stripped to 120° at 2 mmHg to give product.

EXAMPLE 16

Preparation of 4-phenyl-1,2,4-triazoline-3,5-dione

A mixture of 9.8 g of the product of Example 3, 200 ml of dichloromethane and 20 g of $Na_2SO_4$ was cooled to 0° C. with an ice salt bath.

3. $N_2O_4$ was slowly introduced into the reaction medium at −7° to −4° C. until excess $N_2O_4$ was detected.

The mixture was then heated to 0° C. and filtered. The collected solids were washed with 600 ml of dichloromethane.

The filtrate was reduced to 400 ml by vacuum stripping at 10° C. A clear red solution resulted.

EXAMPLE 17

Preparation of 1-alkylene substituted 4-phenyl urazole 1000 g of a 10% weight solution of ethylenepropylene-hexadiene terpolymer (Ortholeum 2052) in chlorobenzene was treated with the triazolinedione solution from Example 16. This new solution was stirred at 20°-25° C. for 22½ hrs. and at 75° for 1 hr. 900 g of diluent oil was then added and the solution stripped to 170° at 3 mmHg. The residue was then filtered at 120° to give the desired product.

EXAMPLE 18

Preparation of 1-polyisobutylene-4-phenyl urazole 800 ml of a solution of 4-phenyltriazolinedione in dichloromethane was prepared from 20 g of the product of Example 3 according to the procedure of Example 16. This solution was then added to a solution of 214.7 g of polyisobutylene (2000 equivalent weight) in 100 ml chlorobenzene. This new solution was then stirred at room temperature for 24 hours. The solution was then heated to 75° C. for 2 hours.

41.2 g of diluent oil was added and the material was stripped to 150° C. at 3 mmHg to give the desired product.

EXAMPLE 19

Preparation of the zinc salt of the product of Example 18

A mixture of 75 g of the product of Example 18, 50 ml of xylene, 50 ml of isobutyl alcohol, 1.19 g of ZnO and 1.76 g of acetic acid was stirred at 110° C. for 1½ hours.

16.5 g of diluent oil was added and the material stripped to 160° C. at 3 mmHg. The residue was filtered through diatomaceous earth filter aid to give the desired product.

EXAMPLE 20

Preparation of oligomer with succinylchloride 2.9 g of succinylchloride was added to a solution of 100 g of the product of Example 18 and 22.1 g of diluent oil heated to 60° C. and the material heated at 120° C. for 1½ hours, 150° C. for 1½ hours and 180° C. for ½ hour. 0.725 g of additional succinylchloride was added and the material heated at 150° C. for 2½ hours. 0.36 g of succinylchloride was further added and the material heated for 2½ hours at 150°. After cooling to 90° C., diatomaceous earth filter aid was added with stirring for ½ hour. After filtration through the filter aid, the desired product was obtained.

EXAMPLE 21

Acetyl Derivative of the Product of Example 17

The product of Example 17 (669 g) was heated to 120° C. under a slow $N_2$ purge.

4.1 g of acetic anhydride was added and the material stirred at 120° C. for 1½ hrs. The material was then heated to 180° C. with a 0.5cfh $N_2$ purge for 1 hr. The material was cooled to obtain the desired product.

EXAMPLE 22

Alkenylation of the Product of Example 5 with Polyisobutylene 20 g of the product of Example 5, 1000 g of dichloromethane and 50 g of $Na_2SO_4$ were admixed and cooled to 3° C. in an ice bath.

6.35 g of $N_2O_4$ was condensed with the above mixture over a 20-min. period. After the above addition was complete, the material was warmed to room temperature over ½ hr. and then maintained at room temperature for ½ hr. The material was filtered and the filtrate reduced to 1000 ml by vacuum stripping at approximately 10° C. to give a clear, red solution.

289.8 g of polyisobutylene (mole weight 2050) and 125 ml chlorobenzene were added to the above red solution. This new solution was stirred for 22 hrs. at room temperature followed by heating to 75° C.

132.7 g of diluent oil was added and the material stripped to 160° C. to obtain the desired product.

EXAMPLE 23

Acylation of the Product of Example 22

100 g of the product of Example 22 was heated to 120° C.

3.33 g of acetic anhydride was added and the material heated at 120° C. for 1 hr. The material was heated to 150° C. and maintained there for ½ hr.

Material was heated to 180° C. with $N_2$ blowing at 0.5cfh for 1 hr. After cooling to 90° C., 2 g of super filtrol was added and after stirring for ½ hr. the material was filtered through diatomaceous earth filter aid.

The filtrate was the desired product.

As previously discussed the urazole compositions, as exemplified above, are useful as seal swell agents, dispersants, dispersant VI improvers and friction modifiers for functional fluids.

For the purposes of the present invention, the use of the urazole compositions as seal swell agents is achieved by preferably dissolving or stably dispersing a urazole composition of the present invention in an oleaginous liquid of lubricating viscosity in an amount effective to cause swelling of seals. That amount is usually about 0.05-20.0 parts (by weight), preferably about 0.1-5.0 parts, per 100 parts of said liquid. Suitable oleaginous liquids include natural and synthetic oils and mixtures thereof, especially oils of the type useful as crankcase lubricating oils for spark-ignited and compression-ignited internal combustion engines, including automobile and truck engines, two-cycle engines, aviation piston engines, marine and railroad diesel engines, as well as gas engines, jet aircraft turbines, stationary power engines and turbines and the like. Base liquids for automatic transmission fluids, transaxle lubricants, gear lubricants, metal-working lubricants, hydraulic fluids and other lubricating oil and grease compositions are also useful for this purpose.

The invention also includes concentrates for formulating lubricating compositions. Such concentrates comprise a normally liquid, substantially inert organic solvent/diluent and from about 1 to about 99 percent by weight of a urazole composition as hereinabove described.

Natural oils include animal oils and vegetable oils (e.g., castor oil, lard oil) as well as liquid petroluem oils and solvent-treated or acid-treated mineral lubricating oils of the paraffinic, naphthenic or mixed paraffinicnapthenic types, such mineral oils are preferred. Oils of lubricating viscosity derived from coal or shale are also useful.

Synthetic lubricating oils include hydrocarbon oils and halo-substituted hydrocarbon oils such as polymerized and interpolymerized olefins [e.g., polybutylenes, polypropylenes, propylene-isobutylene copolymers, chlorinated polybutylenes, poly(1-hexenes), poly(1-octenes), poly(1-decenes), etc., and mixtures thereof]; alkylbenzenes (e.g., dodecylbenzenes, tetradecylbenzenes, dinoulbenzenes, di-(2-ethylhexyl)benzenes, etc.); polyphenyls (e.g., biphenyls, terphenyls, alkylated polyphenyls, etc.), alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc. constitute another class of known synthetic oils. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, esters, or the $C_{13}$oxo acid diester of tetraethylene glycol.

Another suitable class of synthetic oils comprises the esters of dicarboxylic acids (e.g., phtalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol diethylene glycol monoether, propylene glycol, etc.). Specific examples of these esters include dibutyl adipate, di(2-ethylhexyl)sebavate, din-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic oils [e.g., tetraethyl silicate, tetraisopropyl silicate, tetra-(2-ethylhexyl) silicate, tetra-(4-methyl-2-ethylhexyl) silicate, tetra-(p-tert-butylphenyl) silicate, hexyl-(4-methyl-2-pentoxy) disiloxane, poly(methyl) siloxanes, poly(methylphenyl) siloxanes, etc.]. Other synthetic oils include liquid esters of phosphorus-containing acids (e.g., tricresyl phosphate, trioctyl phosphate, diethyl ester of decylphosphonic acid, etc.), polymeric tetrahydrofurans and the like.

Unrefined, refined and rerefined oils (and mixtures of each with each other) of the type disclosed hereinabove can be used as oleaginous liquids according to the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, acid or base extraction, filtration, percolation, etc. Rerefined oils are obtained by processes similar to those used to obtain refined oils applied to refined oils which have been already used in service. Such refined oils are also known as reclaimed or reprocessed oils and often are additionally processed by techniques directed to removal of spent additives and oil breakdown products.

Other additives may be used in the oleaginous liquid in combination with the specific urazole compositions. Such additives include, for example, detergents and dispersants of the ash-containing or ashless type, corrosion- and oxidation-inhibiting agents, pour point depressing agents, extreme pressure agents, viscosity index improvers, color stabilizers and anti-foam agents.

The ash-containing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloirde, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed method for preparing the basic salts involve heating a mineral oil solution of an acid with a stoichiometric excess of a metal neutralizing agent such as the metal oxide, hydroxide, carbonate, bicarbonate, or sulfide at a temperature above 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, actyl alcohol, cellosolve, carbitol, ethylene glycol, stearyl alcohol, and cyclohexyl alcohol; and amines such as aniline, phenylenediamine, phenothiazine, phenyl-betanaphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200° C.

Ashless detergents and dispersants are illustrated by the interpolymers of an oil-solubilizing monomer, e.g., decyl methacrylate, vinyl decyl ether, or high molecular weight olefin, with a monomer containing polar substituents, e.g., aminoalkyl acrylate or poly-(oxyethylene)-substituted acrylate; the amine salts, amides, and imides of oil-soluble monocarboxylic or dicarboxylic acids such as stearic acid, oleic acid, tall oil acid, and high molecular weight alkyl or alkenyl-substituted succinic acid. Especially useful as ashless detergents are the acylated polyamines and similar nitrogen compounds containing at least about 54 carbon atoms as described in U.S. Pat. No. 3,272,746; reaction products of such compounds with other reagents including boron compounds, phosphorus compounds, epoxides, aldehydes, organic acids and the like; and esters of hydrocarbon-substituted succinic acids as described in U.S. Pat. No. 3,381,022.

Extreme pressure agents and corrosion-inhibiting and oxidation-inhibiting agents are exemplified by chlorinated aliphatic hydrocarbons such as chlorinated wax; organic sulfides and polysulfides such as benzyl disulfide, bis(chlorobenzyl) disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl-hexyl phosphite, pentyl phenyl phosphite, dipentyl phenyl phosphite, tridecyl phosphite, distearyl phosphite, dimethyl naphthyl phosphite, oleyl 4-pentylphenyl phosphite, polypropylene (molecular weight 500) substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)-phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

SEAL SWELL TEST

Urazole compositions formulated in an ATF as discussed above were tested in the GM DEXRON® II Seal Test. The urazole product of Example 1 exhibited a percent seal swell of 11.2%.

FRICTION MODIFICATION

The urazole compositions of the present invention may also be used as friction modifiers or fuel economy agents in lubricants and fuels. The urazole compositions may be formulated similarly in the oils and lubricants as discussed above relative to seal swell agents for use in an internal combustion engine.

The urazole products of Example 1, Example 10 and Example 14 were formulated in a motor oil and tested in the Buick FHP.

The motor oil formulated with the product of Example 1 showed an improvement of 4%, the oil formulated with the product of Example 10 showed a 3.5% improvement and the oil formulated with the product of Example 14 showed a 5.6% improvement in this test.

Moreover, the lubricant compositions of the present invention may be in the form of lubricating oils and greases in which any of the above-described oils of lubricating viscosity may be employed as a vehicle. Where the lubricant is to be used in the form of a grease, the lubricating oil generally is employed in an amount sufficient to balance the total grease composition and generally, the grease compositions will contain various quantities of thickening agents and other additive components to provide desirable properties.

A wide variety of thickening agents can be used in the preparation of the greases of this invention. Included among the thickening agents are alkali and alkaline earth metal soaps of fatty acids and fatty materials having from about 12 to about 30 carbon atoms. The metals are typified by sodium, lithium, calcium and barium. Examples of fatty materials include stearic acid, hydroxy stearic acid, stearin, oleic acid, palmetic acid, myristic acid, cottonseed oil acids, and hydrogenated fish oils.

Other thickening agents include salt and salt-soap complexes as calcium stearate-acetate (U.S. Pat. No. 2,197,263), barium stearate acetate (U.S. Pat. No. 2,564,561), calcium stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Particularly useful thickening agents employed in the grease compositions are essentially hydrophilic in character, but which have been converted into a hydrophobic condition by the introduction of long chain hydrocarbon radicals onto the surface of the clay particles prior to their use as a component of a grease composition, as, for example, by being subjected to a preliminary treatment with an organic cationic surface-active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, and is believed to require no further discussion. More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum silicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is employed in an amount from about 0.5 to about 30, and preferably from 3% to 15% by weight of the total grease composition.

The invention also includes aqueous compositions characterized by an aqueous phase with at least one amine and/or metal salt of at least one urazole composition of the invention dispersed or dissolved in said aqueous phase. Preferably, this aqueous phase is a continuous aqueous phase although, in some embodiments, the aqueous phase can be a discontinuous phase. These aqueous compositions usually contain at least about 25% by weight water. Such aqueous compositions encompass both concentrates containing about 25% to about 80% by weight, preferably from about 40% to about 65% water; and water-based functional fluids containing generally over about 80% by weight of water. The concentrates generally contain from about 10% to about 90% by weight of at least one urazole composition (I). The concentrates generally contain less than about 50%, preferably less than about 25%, more preferably less than about 15%, and still more preferably less than about 6% hydrocarbon oil. The water-based functional fluids generally contain less than about 15%, preferably less than about 5%, and more preferably less than about 2% hydrocarbon oil.

These concentrates and water-based functional fluids can optionally include other conventional additives commonly employed in water-based functional fluids. These other additives include surfactants; thickeners; oil-soluble, water-insoluble functional additives such as antiwear agents, extreme pressure agents, dispersants, etc.; and supplemental additives such as corrosion-inhibitors, shear stabilizing agents, bactericides, dyes, water-softeners, odor masking agents, antifoam agents and the like.

The concentrates are analogous to the water-based functional fluids except except that they contain less water and proportionately more of the other ingredients. The concentrates can be converted to water-based functional fluids by dilution with water. This dilution is usually done by standard mixing techniques. This is often a convenient procedure since the concentrate can be shipped to the point of use before additional water is added. Thus, the cost of shipping a substantial amount of the water in the final water-based functional fluid is saved. Only the water necesssary to formulate the concentrate (which is determined primarily be ease of handling and convenience factors), need be shipped.

Generally these water-based functional fluids are made by diluting the concentrates with water, wherein the ratio of water to concentrate is usually in the range of about 80:20 to about 99:1 by weight. As can be seen when dilution is carried out within these ranges, the final water-based functional fluid contains, at most, an insignificant amount of hydrocarbon oil.

In various preferred embodiments of the invention, the water-based functional fluids are in the form of solutions while in other embodiments they are in the form of micelle dispersions or microemulsions which appear to be true solutions. Whether a solution, micelle dispersion or microemulsion is formed is dependent, inter alia, on the particular components employed.

Also included within this invention are methods for preparing aqueous compositions, including both concentrates and water-based functional fluids, containing other conventional additives commonly employed in water-based functional fluids. These methods comprise the steps of:

(1) mixing at least one urazole composition (I) of the invention with such other conventional additives either simultaneously or sequentially to form a dispersion or solution; optionally (2) combining said dispersion or solution with water to form said aqueous concentrate; and/or (3) diluting said dispersion or solution, or concentrate with water wherein the total amount of water used is in the amount required to provide the desired concentration of the components of the invention and other functional additives in said concentrates or said water-based functional fluids.

These mixing steps are preferably carried out using conventional equipment and generally at room or slightly elevated temperatures, usually below 100° C. and often below 50° C. As noted above, the concentrate can be formed and then shipped to the point of use where it is diluted with water to form the desired water-based functional fluid. In other instances, the finished water-based functional fluid can be formed directly in the same equipment used to form the concentrate or the dispersion or solution.

The surfactants that are useful in the aqueous compositions of the invention can be of the cationic, anionic, nonionic or amphoteric type. Many such surfactants of each type are know to the art. See, for example, McCutcheon's "Emulsifiers & Detergents," 1981, North American Edition, published by McCutcheon Division, MC Publishing Co., Glen Rock, N.J., U.S.A., which is hereby incorporated by reference for its disclosures in this regard.

Among the nonionic surfactant types are the alkylene oxide-treated products, such as ethylene oxide-treated phenols, alcohols, esters, amines and amides. Ethylene oxide/propylene oxide block copolymers are also useful nonionic surfactants. Glycerol esters and sugar esters are also known to be nonionic surfactants. A typical nonionic surfactant class useful with the present invention are the alkylene oxide-treated alkyl phenols such as the ethylene oxide alkyl phenol condensates sold by the Rohm & Haas Company. A specific example of these is Triton X-100 which contains an average of 9-10 ethylene oxide units per molecule, has an HLB value of about 13.5 and a molecular weight of about 628. Many other suitable nonionic surfactants are known; see, for example, the aforementioned McCutcheon's as well as the treatise "Non-Ionic Surfactants" edited by Martin J. Schick, M. Dekker Co., New York, 1967, which is herein incorporated by reference for its disclosures in this regard.

As noted above, cationic, anionic and amphoteric surfactants can also be used. Generally, these are all hydrophilic surfactants. Anionic surfactants contain negatively charged polar groups while cationic surfactants contain positively charged polar groups. Amphoteric dispersants contain both types of polar groups in the same molecule. A general survey of useful surfactants is found in Kirk-Othmer Encyclopedia of Chemical Technology, Second Edition, Volume 19, page 507 et seq. (1969, John Wiley and Son, New York) and the aforementioned compilation published under the name of McCutcheon's. These references are both hereby incorporated by reference for their disclosures relating to cationic, amphoteric and anionic surfactants.

Among the useful anionic surfactant types are the widely known carboxylate soaps, organo sulfates, sulfonates, sulfocarboxylic acids and their salts, and phosphates. Useful cationic surfactants include nitrogen compounds such as amine oxides and the well-known quaternary ammonium salts. Amphoteric surfactants include amino acid-type materials and similar types. Various cationic, anionic and amphoteric dispersants are available from the industry, particularly from such companies as Rohm & Haas and Union Carbide Corporation, both of America. Further information about anionic and cationic surfactants also can be found in the texts "Anionic Surfactants," Parts II and III, edited by W. M. Linfield, published by Marcel Dekker, Inc., New York, 1976, and "Cationic Surfactants," edited by E. Jungermann, Marcel Dekker, Inc., New York, 1976. Both of these references are incorporated by reference for their disclosures in this regard.

These surfactants, when used, are generally employed in effective amounts to aid in the dispersal of the various additives, particularly the functional additives discussed below, in the concentrates and water-based functional fluids of the invention. Preferably, the concentrates can contain up to about 75% by weight, more preferably from about 10% to about 75% by weight of one or more of these surfactants. The water-based functional fluids can contain up to about 15% by weight, more preferably from about 0.05% to about 15% by weight of one or more of these surfactants.

Often the aqueous compositions of this invention contain at least one thickener for thickening said compositions. Generally, these thickeners can be polysaccharides, synthetic thickening polymers, or mixtures of two or more of these. Among the polysaccharides that are useful are natural gums such as those disclosed in "Industrial Gums" by Whistler and B. Miller, published by Academic Press, 1959. Disclosures in this book relating to water-soluble thickening natural gums in hereby incorporated by reference. Specific examples of such gums are gum agar, guar gum, gum arabic, algin, dextrans, xanthan gum and the like. Also among the polysaccharides that are useful as thickeners for the aqueous compositions of this invention are cellulose ethers and esters, including hydroxy hydrocarbyl cellulose and hydrocarbylhydroxy cellulose and it salts. Specific examples of such thickeners are hydroxyethyl cellulose and the sodium salt of carboxymethyl cellulose. Mixtures of two or more of any such thickeners are also useful.

It is a general requirement that the thickener used in the aqueous compositions of the present invention be soluble in both cold (10° C.) and hot (about 90° C.) water. This excludes such materials as methyl cellulose which is soluble in cold water but not in hot water. Such hot-water-insoluble materials, however, can be used to perform other functions such as providing lubricity to the aqueous compositions of this invention.

These thickeners can also be synthetic thickening polymers. Many such polymers are known to those of skill in the art. Representative of them are polyacrylates, polyacrylamides, hydrolyzed vinyl esters, water-soluble homo- and interpolymers of acrylamidoalkane sulfonates containing 50 mole percent at least of acryloamido alkane sulfonate and other comonomers such as acrylonitrile, styrene and the like. Poly-n-vinyl pyrrolidones, homo- and copolymers as well as water-soluble salts of styrene, maleic anhydride and isobutylene maleic anhydride copolymers can also be used as thickening agents.

Other useful thickeners are known to those of skill in the art and many can be found in the list in the aforementioned McCutcheon Publication: "Functional Materials," 1976, pp. 135–147, inclusive. The disclosures therein, relative to water-soluble polymeric thickening agents meeting the general requirements set forth above are hereby incorporated by reference.

Preferred thickeners, particularly when the compositions of the invention are required to be stable under high shear applications, are the water-dispersible reaction products formed by reacting at least one hydrocarbyl-substituted succinic acid and/or anhydride represented by the formula

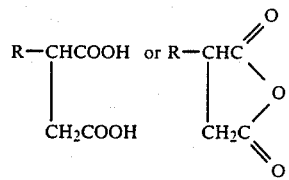

wherein R is a hydrocarbyl group of from about 8 to about 40 carbon atoms, with at least one water-dispersible amine terminated poly(oxyalkylene) or at least one water-dispersible hydroxy-terminated polyoxyalkylene. R preferably has from about 8 to about 30 carbon atoms, more preferably from about 12 to about 24 carbon atoms, still more preferably from about 16 to about 18 carbon atoms. In a preferred embodiment, R is represented by the formula

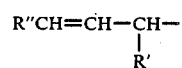

wherein R' and R" are independently hydrogen or straight chain or substantially straight chain hydrocarbyl groups, with the proviso that the total number of carbon atoms in R is within the above-indicated ranges. Preferably R' and R" are alkyl or alkenyl groups. In a particularly advantageous embodiment, R has from about 16 to about 18 carbon atoms, R' is hydrogen or an alkyl group of from 1 to about 7 carbon atoms or an alkenyl group of from 2 to about 7 carbon atoms, and R" is an alkyl or alkenyl group of from about 5 to about 15 carbon atoms.

The water-dispersible amine terminated poly(oxyalkylene)s are preferably alpha omega diamino poly(oxyethylene)s, alpha omega diamino poly(oxypropylene) poly(oxyethylene) poly(oxypropylene)s or alpha omega diamino propylene oxide capped poly(oxyethylene)s. The amine-terminated poly(oxyalkylene) can also be a urea condensate of such alpha omega diamino poly(oxytheylene)s, alpha omega diamino poly(oxypropylene) poly(oxyethylene) poly(oxypropylene)s or alpha omega diamino propylene oxide capped poly(oxyethylene)s. The amine-terminated poly(oxyalkylene) can also be a polyamine (e.g., triamino, tetramino, etc.) polyoxyalkylene provided it is amine-terminated and it is water-dispersible.

Examples of water-dispersible amine-terminated poly(oxyalkylene)s that are useful in accordance with the present invention are disclosed in U.S. Pat. Nos. 3,021,232; 3,108,011; 4,444,566; and RE 31,522. The disclosures of these patents are incorporated herein by reference. Water-dispersible amine terminated poly(oxyalkylene)s that are useful are commercially available from the Texaco Chemical Company under the trade name "Jeffamine."

The water-dispersible hydroxy-terminated polyoxyalkylenes are constituted of block polymers of propylene oxide and ethylene oxide, and a nucleus which is derived from organic compounds containing a plurality of reactive hydrogen atoms. The block polymers are attached to the nucleus at the sites of the reactive hydrogen atoms. Examples of these compounds include the hydroxy-terminated polyoxyalkylenes which are represented by the formula

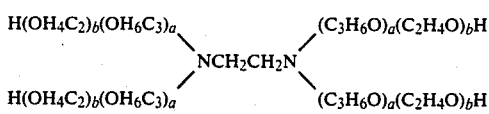

wherein a and b are integers such that the collective molecular weight of the oxypropylene chains range from about 900 to about 25,000, and the collective weight of the oxyethylene chains constitute from about 20% to about 90%, preferably from about 25% to about 55% by weight of the compound. These compounds are commercially available from BASF Wyandotte Corporation under the trade name "Tetronic." Additional examples include the hydroxy-terminated polyoxyalkylenes represented by the formula

wherein y is an integer such that the molecular weight of the oxypropylene chain is at least about 900, and x and z are integers such that the collective weight of the oxyethylene chains constitute from about 20% to about 90% by weight of the compound. These compounds preferably have a molecular weight in the range of about 1,100 to about 14,000. These compounds are commercially available from BASF Wyandotte Corporation under the trade name "Pluronic." Useful hydroxy-terminated polyoxyalkylenes are disclosed in U.S. Pat. Nos. 2,674,619 and 2,979,528, which are incorporated herein by reference.

The reaction between the carboxylic agent and the amine- or hydroxy-terminated polyoxyalkylene can be carried out at a temperature ranging from the highest of the melt temperatures of the reaction components up to the lowest of the decomposition temperatures of the reaction components or products. Generally, the reaction is carried out at a temperature in the range of about 60° C. to about 160° C., preferably about 120° C. to about 160° C. The ratio of equivalents of carboxylic agent to polyoxyalkylene preferably ranges from about 0.1:1 to about 8:1, preferably about 1:1 to about 4:1, and advantageously about 2:1. The weight of an equivalent of the carboxylic agent can be determined by dividing its molecular weight by the number of carboxylic functions present. The weight of an equivalent of the amine-terminated polyoxyalkylene can be determined by dividing its molecular weight by the number of terminal amine groups present. The weight of an equivalent of the amine-terminated polyoxyalkylene can be determined by dividing its molecular weight by the number of terminal amine groups present. The number of terminal amine and hydroxyl groups can usually be determined from the structural formula of the polyoxyalkylene or empirically through well-known procedures. The amine/acids and ester/acids formed by the reaction of the carboxylic agent and amine-terminated or hydroxy-terminated polyoxyalkylene can be neutralized with, for example, one or more alkali meals, one or more amines, or a mixture thereof, and thus converted to amide/salts or ester/salts, respectively. Additionally, if these amide/acids or ester/acids are added to concentrates or functional fluids containing alkali metals or amines, amide/salts or ester/salts usually form, in situ.

South African Pat. No. 85/0978 is incorporated herein by reference for its teachings with respect to the use of hydrocarbyl-substituted succinic acid or anhydride/hydroxy-terminated poly(oxyalkylene) reaction products as thickeners for aqueous compositions.

When the thickener is formed using an amine-terminated poly(oxyalkylene), the thickening characteristics of said thickener can be enhanced by combining it with at least one surfactant. Any of the surfactants identified above under the subtitle "Surfactants" can be used in this regard. When such surfactants are used, the weight ratio of thickener to surfactant is generally in the range of from about 1:5 to about 5:1, preferably from about 1:1 to about 3:1.

Typically, the thickener is present in a thickening amount in the aqueous compositions of this invention. When used, the thickener is preferably present at a level of up to about 70% by weight, preferably from about 20% to about 50% by weight of the concentrate of the invention. The thickener is preferably present at a level in the range of from about 1.5% to about 10% by weight, preferably from about 3% to about 6% by weight of the functional fluids of the invention.

The functional additives that can be used in the aqueous systems are typically oil-soluble, water-insoluble additives which function in conventional oil-based systems as extreme pressure agents, antiwear agents, load-carrying agents, dispersants, friction modifiers, lubricity agents, etc. They can also function as anti-slip agents, film formers and friction modifiers. As is well known, such additives can function in two or more of the above-mentioned ways; for example, extreme pressure agents often function as load-carrying agents.

The term "oil-soluble, water-insoluble functional additive" refers to a functional additive which is not soluble in water above a level of about 1 gram per 100 milliliters of water at 25° C., but is soluble in mineral oil to the extent of at least 1 gram per liter at 25° C.

These functional additives can also include certain solid lubricants such as graphite, molybdenum disulfide and polytetrafluoroethylene and related solid polymers.

These functional additives can also include frictional polymer formers. Briefly, these are potential polymer forming materials which are dispersed in a liquid carrier at low concentration and which polymerize at rubbing or contacting surfaces to form protective polymeric films on the surfaces. The polymerizations are believed to result from the heat generated by the rubbing and, possibly, from catalytic and/or chemical action of the freshly exposed surface. A specific example of such materials is dilinoleic acid and ethylene glycol combinations which can form a polyester frictional polymer film. These materials are known to the art and descriptions of them are found, for example, in the journal "Wear," Volume 26, pages 369–392, and West German Published Patent Application 2,339,065. These disclosures are hereby incorporated by reference for their discussions of frictional polymer formers.

Typically these functional additives are known metal or amine salts of organo sulfur, phosphorus, boron or carboxylic acids which are the same as or of the same type as used in oil-based fluids. Typically such salts are of carboxylic acids of 1 to 22 carbon atoms including both aromatic and aliphatic acids; sulfur acids such as alkyl and aromatic sulfonic acids and the like; phosphorus acids such as phosphoric acid, phosphorus acid, phosphinic acid, acid phosphate esters and analogous sulfur homologs such as the thiophosphoric and dithiophosphoric acid and related acid esters; boron acids include boric acid, acid borates and the like. Useful functional additives also include metal dithiocarbamates such as molybdenum and tributyl tin oxide, phosphates and phosphites; borate amine salts, chlorinated waxes; trialkyl tin oxide, molybdenum phosphates, and chlorinated waxes.

Many such functional additives are known to the art. For example, descriptions of additives useful in conventional oil-based systems and in the aqueous systems of this invention are found in "Advances in Petroleum Chemistry and Refining," Volume 8, edited by John J. McKetta, Interscience Publishers, New York, 1963, pages 31–38 inclusive; Kirk-Othmer "Encyclopedia of chemical Technology," Volume 12, Second Edition, Interscience Publishers, New York, 1967, page 575 et seq.; "Lubricant Additives" by M. W. Ranney, Noyes Data Corporation, Park Ridge, N.J., U.S.A., 1973; and "Lubricant Additives" by C. V. Smalheer and R. K. Smith, The Lezius-Hiles Co., Cleveland, Ohio, U.S.A. These references are hereby incorporated by reference for their disclosures of functional additives useful in the compositions of this invention.

In certain of the type aqueous compositions of the invention, the functional additive is a sulfur or chlorosulfur extreme pressure agent, known to be useful in oil-base systems. Such materials include chlorinated aliphatic hydrocarbons, such as chlorinated wax; organic sulfides and polysulfides, such as benzyl-disulfide, bis-(chlorobenzyl)disulfide, dibutyl tetrasulfide, sulfurized sperm oil, sulfurized methyl ester of oleic acid, sulfurized alkylphenol, sulfurized dipentene, sulfurized terpene, and sulfurized Diels-Alder adducts; phosphosulfurized hydrocarbons, such as the reaction product of phosphorus sulfide with turpentine or methyl oleate; phosphorus esters such as the dihydrocarbon and trihydrocarbon phosphites, i.e., dibutyl phosphite, diheptyl phosphite, dicyclohexyl phosphite, pentylphenyl phosphite, dipentylphenyl phosphite, tridecyl phosphite, distearyl phosphite and polypropylene substituted phenol phosphite; metal thiocarbamates, such as zinc dioctyldithiocarbamate and barium heptylphenol dithiocarbamate; and Group II metal salts of a phosphorodithioic acid, such as zinc dicyclohexyl phosphorodithioate.

The functional additive can also be a film former such as a synthetic or natural latex or emulsion thereof in water. Such latexes include natural rubber latexes and polystyrene butadienes synthetic latex.

The functional additive can also be an anti-chatter or anti-squawk agent. Examples of the former are the amide metal dithiophosphate combinations such as disclosed in West German Pat. No. 1,109,302; amine salt-azomethane combinations such as disclosed in British Patent Specification No. 893,977; or amine dithiophosphate such as disclosed in U.S. Pat. No. 3,002,014. Examples of anti-squawk agents are N-acyl-sarcosines and derivatives thereof such as disclosed in U.S. Pat Nos. 3,156,652 and 3,156,653; sulfurized fatty acids and esters thereof such as disclosed in U.S. Pat. Nos. 2,913,415 and 2,982,734; and esters of dimerized fatty acids such as disclosed in U.S. Pat. No. 3,039,967. The above-cited patents are incorporated herein by reference for their disclosure as pertinent to anti-chatter and anti-squawk agents useful as a functional additive in the aqueous systems of the present invention.

Specific examples of functional additives useful in the aqueous systems of this invention include the following commercially available products.

TABLE I

| Functional Additive Trade Name | Chemical Description | Supplier |
|---|---|---|
| Anglamol 32 | Chlorosulfurized hydrocarbon | Lubrizol[1] |
| Anglamol 75 | Zinc dialkyl phosphate | Lubrizol[1] |
| Molyvan L | A thiaphosphomolybdate | Vanderbilt[2] |
| Lubrizol-5315 | Sulfurized cyclic carboxylate ester | Lubrizol[1] |
| Emcol TS 230 | Acid phosphate ester | Witco[3] |

[1]The Lubrizol Corporation, Wickliffe, Ohio, U.S.A.
[2]R. T. Vanderbilt Company, Inc., New York, New York, U.S.A.
[3]Witco Chemical Corp., Organics Division, Houston, Texas, U.S.A.

Mixtures of two or more of any of the afore-described functional additives can also be used.

Typically, a functionally effective amount of the functional additive is present in an aqueous compositions of this invention.

The term "functionally effective amount" refers to a sufficient quantity of an additive to impart desired properties intended by the addition of said additive. For example, if an additive is a rust-inhibitor, a functionally effective amount of said rust-inhibitor would be an amount sufficient to increase the rust-inhibiting characteristics of the composition to which it is added. Similarly, if the additive is an antiwear agent, a functionally effective amount of said antiwear agent would be a sufficient quantity of the antiwear agent to improve the antiwear characteristics of the composition to which it is added.

The aqueous system of this invention often contain at least one inhibitor for corrosion of metals. These inhibitors can prevent corrosion of either ferrous or non-ferrous metals (e.g., copper, bronze, brass, titanium, aluminum and the like) or both. The inhibitor can be organic or inorganic in nature. Usually it is sufficiently soluble in water to provide a satisfactory inhibiting action though it can function as a corrosion-inhibitor without dissolving in water, it need not be water-soluble. Many suitable inorganic inhibitors useful in the aqueous systems of the present invention are known to those skilled in the art. Included are those described in "Protective Coatings for Metals" by Burns and Bradley, Reinhold Publishing Corporation, Second Edition, Chapter 13, pages 596–605. This disclosure relative to inhibitors are hereby incorporated by reference. Specific examples of useful inorganic inhibitors include alkali metal nitrites, sodium di- and tripolyphosphate, potassium and dipotassium phosphate, alkali metal borate and mixtures of the same. Many suitable organic inhibitors are known to those of skill in the art. Specific examples include hydrocarbyl amine and hydroxy-substituted hydrocarbyl amine neutralized acid compound, such as neutralized phosphates and hydrocarbyl phosphate esters, neutralized fatty acids (e.g., those having about 8 to about 22 carbon atoms), neutralized aromatic carboxylic acids (e.g., 4-tertiarybutyl benzoic acid), neutralized naphthenic acids and neutralized hydrocarbyl sulfonates. Mixed salt esters of alkylated succinimides are also useful. Particularly useful amines include the alkanol amines such as ethanol amine, diethanolamine. Mixtures of two or more of any of the afore-described corrosion-inhibitors can also be used. The corrosion-inhibitor is usually present in concentrations in which they are effective in inhibiting corrosion of metals with which the aqueous composition comes in contact.

Certain of the aqueous systems of the present invention (particularly those that are used in cutting or shaping of metal) can also contain at least one polyol with inverse solubility in water. Such polyols are those that become less soluble as the temperature of the water increases. They thus can function as surface lubricity agents during cutting or working operations since, as the liquid is heated as a result of friction between a metal workpiece and work tool, the polyol of inverse solubility "plates out" on the surface of the workpiece, thus improving its lubricity characteristics.

The aqueous systems of the present invention can also include at least one bactericide. Such bactericides are well known to those of skill in the art and specific examples can be found in the afore-mentioned McCutcheon publication "Functional Materials" under the heading "Antimicrobials" on pages 9–20 thereof. This disclosure is hereby incorporated by reference as it relates to suitable bactericides for use in the aqueous compositions or systems of this invention. Generally, these bactericides are water-soluble, at least to the extent to allow them to function as bactericides.

The aqueous system of the present invention can also include such other materials as dyes, e.g., an acid green dye; water softeners, e.g., ethylene diamine tetraacetate sodium salt or nitrilo triacetic acid; odor masking agents, e.g., citronella, oil of lemon, and the like; and anti-foamants, such as the well-known silicon anti-foamant agents.

The aqueous system of this invention may also include an antifreeze additive where it is desired to use the composition at a low temperature. Materials such as ethylene glycol and analogous polyoxyalkylene polyols can be used as antifreeze agents. Clearly, the amount used will depend on the degree of antifreeze protection desired and will be known to those of ordinary skill in the art.

It should also be noted that many of the ingredients described above for use in making the aqueous systems of this invention are industrial products which exhibit or confer more than one property on such aqueous compositions. Thus, a single ingredient can provide several functions thereby eliminating or reducing the need for some other additional ingredient. Thus, for example, an extreme pressure agent such as tributyl tin oxide can also function as a bactericide.

While the invention has been described and illustrated with reference to certain preferred embodiments thereof, those skilled in the art will appreciate that various changes, modifications and substitutions can be made therein without departing from the spirit of the invention. For example, different concentration ranges other than the preferred ranges set forth hereinabove may be applicable as a consequence of variations in the oil base stock or the type of engine or the like. It is intended, therefore, that the invention be limited only by the scope of the claims which follow.

What is claimed is:

1. A lubricating composition comprising a major amount of an oil or lubricating viscosity and about 0.05 to 20 percent by weight of an additive defined by the formula:

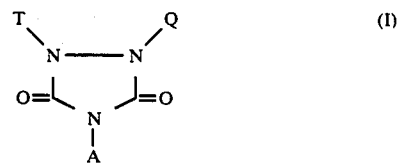

wherein T and Q may be the same or different and represent hydrogen, hydrocarbyl, sulfur, phosphorus, boron, a metal cation, acyloxy hydrocarbyl, imido hydrocarbyl, hydrocarbyl repeating units, hydrocarbyl urazole (I) containing repeating units, an acyl urazole repeating units, an acyl group, or hydrocarbyl acyl containing group, a repeating unit of an acyl group, a repeating unit of a hydrocarbyl acyl containing group, or together form a pi bond between the two nitrogen atoms and A is hydrogen, hydrocarbyl, a hydrocarbyl urazole (I) group, a repeating unit of a hydrocarbyl containing acyl group or a repeating unit of a hydrocarbyl containing acyl group which is bonded directly to or through a hydrocarbyl group to another urazole (I) group.

2. The lubricating composition according to claim 1 wherein R is the radical of a fatty acid containing about 10 to about 20 carbon atoms or the radical of an ether containing about 10 to about 20 carbon atoms or hydrocarbylpolyoxyalkylene of about 9 to about 30 carbon atoms wherein said alkylene group contains 1 to about 4 carbon atoms and T and Q are hydrogen.

3. The lubricating composition according to claim 2 wherein A is phenyl, oleyl, octyl, stearyl or isodecyl—O—$(CH_2)_3$—.

4. The lubricating composition of claims 1, 2 or 3 wherein said lubricating composition is an automatic transmission fluid and wherein said additive is present in an amount to effectively cause the swelling of seals of an automatic transmission.

5. A concentrate for formulating lubricating compositions comprising a normally liquid, substantially inert organic solvent/diluent and from about 1% to about 99% by weight of the additive defined in claim 1.

6. A concentrate for formulating lubricating compositions comprising a normally liquid, substantially inert organic solvent/diluent and from about 1% to about 99% by weight of the additive defined in claim 3.

7. A lubricating composition comprising a major amount of an oil of lubricating viscosity and about 0.05 to 20 percent by weight of at least one urazole composition of the formula

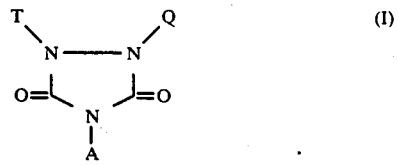

wherein T and Q may be the same or different and represent hydrogen, hydrocarbyl, sulfur, phosphorus, boron, a metal cation, acyloxy hydrocarbyl, imido hydrocarbyl, hydrocarbyl repeating units, hydrocarbyle urazole (I) containing repeating units, an acylurazole repeating units, an acyl group, or hydrocarbyl acyl containing group, a repeating unit of a hydrocarbyl acyl containing group, and A is hydrogen, hydrocarbyl, a hydrocarbyl urazole (I) group, a repeating unit of a hydrocarbyl containing acyl group or a repeating unit of a hydrocarbyl containing acyl group which is bonded directly to or through a hydrocarbyl group and/or to another urazole (I) group; with the proviso that when T and Q are both hydrogen or independently alkylcarbonyl, alkylaminomethylene, A is not hydrogen, alkyl, cycloalkyl, aryl, aralkyl, alkyl carbonyl or alkylaminomethylene.

8. The lubricating composition according to claim 7 wherein said urazole compositions are present in a friction modifying effective amount.

9. The lubricating composition according to claim 7 wherein said urazole compositions are present in a dispersant effective amount.

10. The lubricating composition according to claim 7 wherein T is hydrocarbyl, Q is hydrogen and A is hydrocarbyl, a hydrocarbyl urazole (I) repeating unit, or hydrocarbyl containing acyl group repeating units; or where T and Q are hydrocarbyl containing acyl urazole (I) repeating units, acyl urazole (I) repeating units or hydrocarbyl urazole (I) repeating units and A is hydrocarbyl.

11. The lubricating composition according to claim 7 wherein said urazole composition is

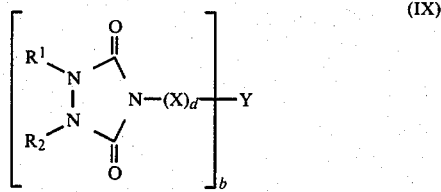
(IX)

wherein $R^1$ and $R^2$ are the same or different and are hydrogen, hydrocarbyl or together form a pi bond between two nitrogen atoms, X is hydrocarbyl, hydrocarbylurazole or acylhydrocarbyl, Y is hydrocarbyl or a urazole group or a linking bond to a repeating unit, d is 0 or at least 1 and b is at least 1; or

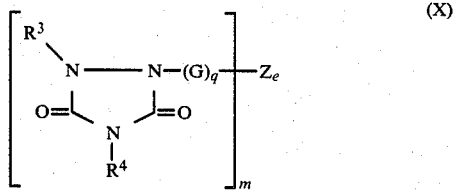
(X)

wherein $R^3$ is independently hydrogen, hydrocarbyl or a linking bond to the group G or Z, $R^4$ is hydrogen, hydrocarbyl acyl, or hydrocarbyl, G is hydrocarbyl, acyl, acyloxy, imido, acyl hydrocarbyl, acyloxy hydrocarbyl, or imido hydrocarbyl, Z is sulfur, phosphorus, boron, a metal cation, or hydrocarbyl, q is 0 or 1, e is 0, 1 or 2 and m is at least 1.

12. The lubricating composition according to claim 11 wherein said urazole is represented by formula IX and wherein $R^1$ and $R^2$ are the same or different and are hydrogen, alkyl or alkenyl of about 8 carbon atoms to about 200 carbon atoms, with the proviso that either $R_1$ or $R_2$ is not hydrogen, and Y is phenyl, oleyl, acetyl or isodecyloxypropyl, and d is 0; or wherein $R^1$ is hydrogen, $R^2$ is alkylene of 1 to about 50 carbon atoms, Y is a linking body with $R^2$, d is 0 and b is at least 1; or wherein $R^1$ and $R^2$ together represent a pi bond between the adjacent nitrogen atoms, Y is alkyl phenylene where said alkyl group is 1 to about 7 carbon atoms, b is 2 and d is 0; or wherein X is arylene, d is 1, Y is alkylene, b is 2 and $R^1$ and $R^2$ are independently hydrogen or hydrocarbyl; or wherein $R^1$ is hydrogen, $R^2$ is hydrogen or hydrocarbyl, Y is arylene or alkylarylene, b is 2 and d is 0; or wherein $R^1$ is hydrogen, $R^2$ is hydrogen or hydrocarbyl, X is arylene, d is 1, Y is alkylene and b is 2; or where $R^1$ is hydrogen or hydrocarbyl, $R^2$ is a linking bond to the repeating unit, Y is a linking bond to the repeating unit, b is at least 2, d is 1 and X is represented by

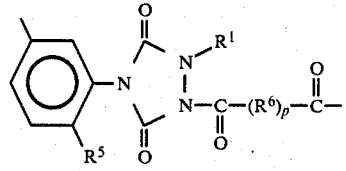

wherein $R^1$ is hydrogen or hydrocarbyl, $R^5$ is hydrocarbyl, $R^6$ is alkylene and p is 0 to about 9.

13. The lubricating composition according to claim 11 wherein said urazole is represented by Formula X and $R^3$ is hydrogen or hydrocarbyl, g is 0, Z is Zn, S or boron, e is 1 or 2, and m is 2 and $R^4$ is phenyl, oleyl, octyl, isodecyloxypropyl or ethylhexyl.

14. The lubricating composition according to claim 11 wherein said urazole is represented by said formula (X) and wherein $R_4$ is hydrocarbyl, G is hydrocarbyl acyl or acyl, q is 1, m is at least 2; $R^3$ is a linking bond of the repeating units and e is 0.

15. A grease composition containing a lubricating composition of any one of claims or 10–14.

* * * * *